United States Patent
Yang et al.

(10) Patent No.: US 11,485,823 B2
(45) Date of Patent: Nov. 1, 2022

(54) POLYMER FOR DELIVERY OF BIOLOGICALLY ACTIVE MATERIALS

(71) Applicant: Agency for Science, Technology and Research, Singapore (SG)

(72) Inventors: Yi-Yan Yang, Singapore (SG); Chuan Yang, Singapore (SG); Wei Cheng, Singapore (SG); Ashlynn Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 346 days.

(21) Appl. No.: 16/627,094

(22) PCT Filed: May 23, 2018

(86) PCT No.: PCT/SG2018/050249
§ 371 (c)(1),
(2) Date: Dec. 27, 2019

(87) PCT Pub. No.: WO2019/004932
PCT Pub. Date: Jan. 3, 2019

(65) Prior Publication Data
US 2020/0165390 A1   May 28, 2020

(30) Foreign Application Priority Data

Jun. 29, 2017   (SG) .............................. 10201705336P (51) Int. Cl.
*C08G 73/02* (2006.01)
*A61K 47/59* (2017.01)

(52) U.S. Cl.
CPC .......... *C08G 73/0206* (2013.01); *A61K 47/59* (2017.08); *C08G 73/0213* (2013.01)

(58) Field of Classification Search
CPC .. A61K 47/549; A61K 47/59; A61K 47/6455; C08G 73/0206; C08G 73/0213; C08G 73/024; C08G 73/0253
See application file for complete search history.

(56) References Cited

U.S. PATENT DOCUMENTS

| 2014/0080215 A1 | 3/2014 | Cheng et al. |
| 2016/0076038 A1 | 3/2016 | Cheng et al. |

FOREIGN PATENT DOCUMENTS

| CN | 1970591 | 5/2007 |
| JP | H05-140213 | 6/1993 |
| JP | H055140213 | * 6/1993 |

OTHER PUBLICATIONS

Englert et al., Facile carbohydrate-mimetic modifications of poly-(ethylene imine) carriers for gene delivery applications. Polymer Chemistry, Sep. 8, 2016;7(37):5862-5872.
Huang et al., Reduction-responsive multifunctional hyperbranched polyaminoglycosides with excellent antibacterial activity, biocompatibility and gene transfection capability. Biomaterials. Nov. 2016;106:134-43. doi: 10.1016/j.biomaterials.2016.08.025. Epub Aug. 17, 2016.
Miryala et al., Parallel Synthesis and Quantitative Structure-Activity Relationship (QSAR) Modeling of Aminoglycoside-Derived Lipopolymers for Transgene Expression. ACS Biomaterials Science & Engineering, May 19, 2015;1(8):656-668.
Potta et al., Discovery of antibiotics-derived polymers for gene delivery using combinatorial synthesis and cheminformatics modeling. Biomaterials. Feb. 2014;35(6): 1977-88. doi: 10.1016/j.biomaterials.2013.10.069. Epub Dec. 10, 2013.
Zhang et al., Lipid-modified aminoglycoside derivatives for in vivo siRNA delivery. Adv Mater. Sep. 6, 2013;25(33):4641-45. doi: 10.1002/adma.201301917. Epub Jun. 27, 2013.

* cited by examiner

*Primary Examiner* — Anna R Falkowitz
(74) *Attorney, Agent, or Firm* — Wolf, Greenfield & Sacks, P.C.

(57) ABSTRACT

The present invention mainly relates to a polymer for delivery of biologically active materials, a complex and a method of synthesis thereof. The polymer comprises a poly(ethylene imine) and at least one monomer, each monomer comprising a modified sugar moiety, preferably galactose, comprising a sulphur atom or a nitrogen atom and a chemical moiety comprising a terminal epoxide for linking the polyethylene imine to the monomer, wherein the sulphur atom or the nitrogen atom links the modified sugar moiety to the chemical moiety. The biologically active material is preferably a gene, siRNA, mRNA or plasmid DNA. Further disclosed is the medical use of said complex in treating a disease caused by a genetic disorder, for example cancer.

20 Claims, 5 Drawing Sheets

POLYMER FOR DELIVERY OF BIOLOGICALLY ACTIVE MATERIALS

RELATED APPLICATIONS

This application is a national stage filing under 35 U.S.C. § 371 of international application number PCT/SG2018/050249, filed May 23, 2018, which claims the benefit of Singapore application serial number 10201705336P, filed Jun. 29, 2017, each of which is herein incorporated by reference in its entirety.

TECHNICAL FIELD

The present invention generally relates to a polymer for delivery of biologically active materials, in particular a polymer comprising poly(ethylene imine), and will be described in this context. The present invention also relates to a complex thereof and a method of synthesizing the same.

BACKGROUND

The following discussion of the background to the invention is intended to facilitate an understanding of the present invention only. It should be appreciated that the discussion is not an acknowledgement or admission that any of the material referred to was published, known or part of the common general knowledge of the person skilled in the art in any jurisdiction as at the priority date of the invention.

A number of non-viral gene delivery systems have been reported, including cationic lipids, polymers and peptides, and conjugation of nucleic acids with natural ligands such as cholesterol as well as cell penetration peptides. In particular, the cationic polymer poly(ethylenimine) (PEI), which contains primary, secondary and tertiary amine groups, provides high gene transfection efficiency in vitro. However, the net positive charge of PEI leads to cytotoxicity, aggregation and undesired non-specific interactions with cellular and non-cellular components in vivo, thereby resulting in liver necrosis, adhesion of aggregated platelets and shock after systemic injection of high doses.

To abrogate the toxic effects, various modifications of PEI have been introduced to alter the PEI/DNA complex architecture and shield PEI surface. Examples include grafting PEI with poly(ethylene glycol) (PEG), hyaluronic acid, chitosan, oligosaccharide, and neutralization of primary amine groups in PEI by hydrophobic or hydrophilic components. However, most of these modifications involve multiple synthesis steps and are therefore, tedious and require significant amounts of time and reagents.

In the past two decades, achieving specific delivery of genes to hepatocytes is an attractive proposition for the treatment of a variety of liver diseases. Galactose is the most studied targeting ligand to liver cells as it is recognized by asialoglycoprotein receptors (ASGP-Rs) on hepatocytes. Galactosylated PEI polymers have been reported as carriers for selectively transfecting hepatocytes. However, there have been disadvantages such as reduced transfection efficiency with increasing N/P ratio, significantly lower transfection efficiency than unmodified PEI and an increase in the size of the complex formed between the galactosylated PEI polymer and a biologically active material, such as DNA. In particular, the increase in size of the complex may make it undesirable for in vivo applications.

In light of the above, there exists a need to develop a polymer for delivering biologically active materials and a complex thereof that can ameliorate or overcome at least one of the above disadvantages.

SUMMARY OF INVENTION

The present invention seeks to provide a polymer for delivering biologically active materials and a complex thereof that addresses the aforementioned need at least in part. The present invention also seeks to provide a method of synthesizing the same.

Accordingly, in an aspect of the present invention, there is provided a polymer comprising a poly(ethylene imine) and at least one monomer, each monomer comprising: (a) a modified sugar moiety comprising a sulphur atom or a nitrogen atom; and (b) a chemical moiety comprising a terminal epoxide for linking the poly(ethylene imine) to the monomer; and wherein the sulphur atom or the nitrogen atom links the modified sugar moiety to the chemical moiety.

Preferably, the modified sugar moiety comprises at least one hydroxyl group, and wherein at least one of the hydroxyl group is a free hydroxyl group.

Preferably, the modified sugar moiety comprises at least one hydroxyl group, and wherein all of the hydroxyl groups are free.

Preferably, the poly(ethylene imine) is a branched poly(ethylene imine).

Preferably, the poly(ethylene imine) is linked to about 10 to about 97 monomers, preferably about 20 to about 70 monomers, and more preferably about 22 monomers, about 41 monomers, about 53 monomers or about 65 monomers.

Preferably, the polymer is water-soluble.

Preferably, the chemical moiety is derived from a diepoxide selected from the group consisting of cyclooctene diepoxide, divinylbenzene diepoxide, 1,7-octadiene diepoxide, 1,3-butadiene diepoxide, 1,4-pentadiene diepoxide, 1,5-hexadiene diepoxide, 1,6-heptadiene diepoxide and the diepoxide of 4-cyclohexenecarboxylate 4-cyclohexenylmethyl ester.

Preferably, the modified sugar moiety is one or more selected from the group consisting of modified mannose, modified galactose, and modified glucose.

In another aspect of the invention, there is provided a method of synthesizing a polymer, the method comprising mixing a poly(ethylene imine) and at least one monomer, each monomer comprising a modified sugar moiety comprising a sulphur atom or a nitrogen atom and a chemical moiety comprising a terminal epoxide for linking the poly(ethylene imine) to the monomer; and wherein the sulphur atom or the nitrogen atom links the modified sugar moiety to the chemical moiety.

Preferably, the modified sugar moiety comprises at least one hydroxyl group, and wherein at least one of the hydroxyl groups is a free hydroxyl group, preferably all the hydroxyl groups are free.

Preferably, the method does not require deprotection.

Preferably, a catalyst is not used.

Preferably, the mixing of the poly(ethylene imine) and the at least one monomer occurs in an aqueous solvent.

Preferably, mixing of the poly(ethylene imine) and the at least one monomer occurs at about 70° C.

Preferably, mixing of the poly(ethylene imine) and the at least one monomer does not require an inert atmosphere.

Preferably, the method further comprises acidification.

Preferably, the monomer is synthesized by reacting a diepoxide with the modified sugar moiety.

Preferably, a base is used as a catalyst and wherein the base is selected from the group consisting of lithium hydroxide, sodium hydroxide and potassium hydroxide.

Preferably, reacting the diepoxide with the modified sugar moiety occurs in a solvent mixture comprising methanol and water.

Preferably, the diepoxide is selected from the group consisting of cyclooctene diepoxide, divinylbenzene diepoxide, 1,7-octadiene diepoxide, 1,3-butadiene diepoxide, 1,4-pentadiene diepoxide, 1,5-hexadiene diepoxide, 1,6-heptadiene diepoxide and the diepoxide of 4-cyclohexenecarboxylate 4-cyclohexenylmethyl ester.

Preferably, mixing the poly(ethylene imine) and the at least one monomer is controlled by changing the molar feed ratio of the poly(ethylene imine) and the at least one monomer.

Preferably, the molar feed ratio is about 10 to about 97, preferably about 20 to about 70, and more preferably about 22, about 41, about 53 or about 65. In another aspect of the invention, there is provided a complex comprising a biologically active material and a polymer as described above.

Preferably, the biologically active material is a nucleic acid, preferably a gene, more preferably siRNA, mRNA or plasmid DNA.

In another aspect of the invention, there is provided a method of treating a cell comprising contacting a cell with the complex as described above.

Preferably, the method is in vitro or in vivo.

Preferably, the cell is a hepatic cell.

In another aspect of the invention, there is provided a complex as described above for use in a treatment, preferably the use is in the treatment of cancer or other diseases caused by a genetic disorder.

Preferably, the use is in the treatment of liver cancer.

In another aspect of the invention, there is provided use of the complex as described above in the manufacture of a medicament for the treatment of cancer, wherein the cancer is liver cancer.

Other aspects of the invention will become apparent to those of ordinary skill in the art upon review of the following description of specific embodiments of the invention in conjunction with the accompanying figures.

BRIEF DESCRIPTION OF FIGURES

The accompanying figures illustrate a non-limiting embodiment or reaction scheme and serve to explain the principles of the disclosed embodiments. The present invention will now be described, by way of example only, with reference to the accompanying figures, in which.

DEFINITIONS

The following words and terms used herein shall have the meaning indicated:

As used herein, the term "biologically active material" includes, but is not limited to, naturally occurring nucleic acids such as DNA and RNA, artificial nucleic acids, prodrugs, pharmaceuticals, small organic molecules, and biomolecules.

As used herein, the term "N/P" refers to the molar ratio of nitrogen of the polymer to phosphorus of the biologically active material (for instance, a gene), and is indicative of the net charge of the complex.

As used herein, the term "Inert atmosphere" refers to a gaseous mixture that contains minimal or no oxygen and comprises of inert gas or gases that have a high threshold before they react. The gaseous mixture may contain nitrogen, argon, helium, carbon dioxide or other inert gases.

As used herein, the term "feed ratio" refers to the molar feed ratio. For instance, a feed ratio of 1:1 refers to equimolar quantities of poly(ethylene imine) and the monomer.

Unless specified otherwise, the terms "comprising", "comprise", and grammatical variants thereof, are intended to represent "open" or "inclusive" language such that they include recited elements but also permit inclusion of additional, unrecited elements. The terms "including", "include", and grammatical variants thereof are construed similarly.

As used herein, the term "about" may refer to +/−5% of the stated value, more preferably +/−4% of the stated value, more preferably +/−3% of the stated value, more preferably +/−2% of the stated value, even more preferably +/−1% of the stated value, and even more preferably +/−0.5% of the stated value.

Throughout this disclosure, certain embodiments may be disclosed in a range format. It should be understood that the description in range format is merely for convenience and brevity and should not be construed as a limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. Ranges are not limited to integers, and can include decimal measurements where applicable. This applies regardless of the breadth of the range.

DETAILED DESCRIPTION

Provided herein is a polymer for delivery of biologically active materials. Exemplary, non-limiting embodiments of the polymer will now be disclosed.

In an aspect of the invention, there is provided a polymer comprising a poly(ethylene imine) and at least one monomer, each monomer comprising a modified sugar moiety comprising a sulphur atom or a nitrogen atom and a chemical moiety comprising a terminal epoxide for linking the poly(ethylene imine) to the monomer, and wherein the sulphur atom or the nitrogen atom links the modified sugar moiety to the chemical moiety.

Advantageously, PEI can be directly grafted to (or reacted with) the polymer without a deprotection step. Consequently, a primary amine group of PEI is converted to a secondary amide group. The functional group(s) of the monomer allows the polymer to form without a deprotection step. In particular, the monomer comprises a modified sugar moiety comprising a sulphur atom or a nitrogen atom, wherein the sulphur atom or the nitrogen atom links the modified sugar moiety to the chemical moiety. In a preferred embodiment, the monomer comprises a modified sugar moiety comprising a sulphur atom.

In various embodiments, the modified sugar moiety is one or more selected from the group consisting of modified mannose, modified galactose, and modified glucose. In a preferred embodiment, the modified sugar moiety is modified galactose. When modified galactose is the modified sugar moiety, one or more of the primary amine groups of PEI may be converted to a secondary amide group.

In various embodiments, the modified sugar moiety comprises at least one hydroxyl group, and wherein at least one of the hydroxyl group is a free hydroxyl group, at least two of the hydroxyl groups are free, or at least three of the hydroxyl groups are free. As such, the modified sugar moiety is partially unprotected. In a preferred embodiment, all of the hydroxyl groups are free. As such, the modified sugar moiety is completely unprotected.

In various embodiments, the poly(ethylene imine) is a linear poly(ethylene imine) or a branched poly(ethylene imine). Due to the limited reactivity of the secondary amines of linear poly(ethylene imine), the grafting number of the galactose would be no more than 20 if linear poly(ethylene imine) is used. In a preferred embodiment, the poly(ethylene imine) is branched. In various embodiments, the average molecular weight of the branched PEI may be in the range of about 1,000 to about 70,000, about 1,000 to about 60,000, about 1,000 to about 50,000, about 1,000 to about 40,000, about 1,500 to about 50,000, about 1,500 to about 40,000, about 1,500 to about 20,000, about 1,500 to about 10,000, about 5,000 to about 15,000, or about 8,000 to about 12,000. In a preferred embodiment, the average molecular weight of the branched PEI is about 10,000.

In various embodiments, the polymer is water-soluble. For instance, the polymer has a solubility of at least 5 mg per 0.7 mL in water. Advantageously, the polymer is water-soluble even when PEI is linked to a number of monomers. In various embodiments, PEI is linked to about 10 to about 97 monomers, about 10 to about 90 monomers, about 10 to about 80 monomers, about 10 to about 70 monomers, about 20 to about 90 monomers, about 20 to about 70 monomers, about 20 to about 65 monomers, preferably about 20 to about 70 monomers, and more preferably about 22 monomers, about 41 monomers, about 53 monomers or about 65 monomers. The number of monomers is calculated based on the $^1$H NMR results of the polymer and rounded to the nearest whole number. In various embodiments, the average molecular weight of the polymer is in the range of about 13,000 to about 42,800. In particular, the average molecular weight of the polymer is 13,380 when the number of monomers is about 10, and the average molecular weight of the polymer is 42,790 when the number of monomers is about 97.

In various embodiments, the chemical moiety comprises a terminal epoxide for linking the poly(ethylene imine) to the monomer. The chemical moiety may further comprise one or more functional groups selected from the group consisting of hydrocarbons (such as alkanes, alkenes, alkynes), halogens (such as chloride, fluorine, bromine), aryls, alcohols, ketones, aldehydes, esters, ethers, amines, amides, thiols, thioethers, disulfides, sulfoxides, phosphates. As such, it should be understood by a person skilled in the art that the chemical moiety may be straight chained or branched, substituted or non-substituted, and/or saturated or unsaturated. In various embodiments, the chemical moiety is derived from a diepoxide selected from the group consisting of cyclooctene diepoxide, divinylbenzene diepoxide, 1,7-octadiene diepoxide, 1,3-butadiene diepoxide, 1,4-pentadiene diepoxide, 1,5-hexadiene diepoxide, 1,6-heptadiene diepoxide and the diepoxide of 4-cyclohexenecarboxylate 4-cyclohexenylmethyl ester. In a preferred embodiment, the diepoxide comprises an alkyl group, such as (but not limited to) 1,3-butadiene diepoxide, 1,4-pentadiene diepoxide, 1,5-hexadiene diepoxide, 1,6-heptadiene diepoxide and 1,7-octadiene diepoxide.

In another aspect of the invention, there is provided a method of synthesizing a polymer, the method comprising mixing a poly(ethylene imine) and at least one monomer, each monomer comprising a modified sugar moiety comprising a sulphur atom or a nitrogen atom and a chemical moiety comprising a terminal epoxide for linking the poly (ethylene imine) to the monomer, and wherein the sulphur atom or the nitrogen atom links the modified sugar moiety to the chemical moiety. Consequently and advantageously, the method may be more environmentally friendly than prior art methods because of the reaction conditions such as, short reaction time, mild reaction conditions, lack of catalyst, and/or use of environmentally friendly solvents.

In various embodiments, the modified sugar moiety comprises at least one hydroxyl group, and wherein at least one of the hydroxyl group is a free hydroxyl group, at least two of the hydroxyl groups are free, or at least three of the hydroxyl groups are free. As such, the modified sugar moiety is partially unprotected. In a preferred embodiment, all of the hydroxyl groups are free. As such, the modified sugar moiety is completely unprotected.

In various embodiments, the method does not require deprotection. This may be because of the absence of protecting groups on at least one of the hydroxyl groups of the modified sugar moiety.

In various embodiments, a catalyst is not used. Advantageously, a catalyst is not necessary for PEI to link to the monomer. As such, there is a savings in cost due to the lack of a catalyst. However, it should be understood that a catalyst, such as (but not limited to) 1,8-Diazabicyclo[5.4.0]undec-7-ene (DBU) may be used.

In various embodiments, the mixing of the poly(ethylene imine) and the at least one monomer occurs in an aqueous solvent. In various embodiments, the aqueous solvent has high polarity and may be selected from the group consisting of water, methanol and a mixture thereof. As such, the method of the present invention may be environmentally friendly compared to prior art methods that use organic solvents, such as chlorinated solvents that may be particularly harmful to the environment. Furthermore, an aqueous solvent such as water may be cheaper than organic solvents. Consequently, there is a savings in cost.

In various embodiments, mixing of the poly(ethylene imine) and the at least one monomer occurs at relatively mild reaction temperatures, such as about 70° C. As such, the method of the present invention may be easier to carry out as compared to, for instance, reflux conditions. In particular, it would not be necessary to set up equipment for reflux, thereby leading to a savings in time.

In various embodiments, mixing of the poly(ethylene imine) and the at least one monomer does not require an inert atmosphere. Advantageously, an inert atmosphere is not required because mixing of the poly(ethylene imine) and the at least one monomer occurs in an aqueous solvent. In contrast, prior art methods that use organic solvents, such as chlorinated solvents, may require an inert atmosphere. This may be because when organic solvents are used, the poly (ethylene imine) can precipitate out of the solvent after absorbing some moisture from the surroundings. As such, an inert atmosphere is required to prevent the poly(ethylene imine) from absorbing moisture in the air. Furthermore, the solubility of the poly(ethylene imine) may become poor in the organic solvent because a part of the poly(ethylene imine) may become protonated. Therefore, as an inert atmosphere is not required for the present invention, mixing of the poly(ethylene imine) and the at least one monomer is convenient, easier to operate and there are cost savings in not requiring costly inert gases.

In various embodiments, the method further comprises acidification. Diluted aqueous acid solutions such as hydrochloric acid (HCl) or sulphuric acid ($H_2SO_4$) may be used for the acidification.

In various embodiments, the monomer is synthesized by reacting a diepoxide with the modified sugar moiety. In various embodiments, the diepoxide is selected from the group consisting of cyclooctene diepoxide, divinylbenzene diepoxide, 1,7-octadiene diepoxide, 1,3-butadiene diepoxide, 1,4-pentadiene diepoxide, 1,5-hexadiene diepoxide, 1,6-heptadiene diepoxide and the diepoxide of 4-cyclohexenecarboxylate 4-cyclohexenylmethyl ester.

In various embodiments, a base is used as a catalyst for reacting the diepoxide with the modified sugar moiety to form a monomer. The base may be selected from the group consisting of lithium hydroxide (LiOH), potassium hydroxide (KOH), potassium methoxide ($KOCH_3$), potassium t-Butoxide (KO(t-Bu)), potassium hydride (KH), sodium hydroxide (NaOH), sodium t-Butoxide (NaO(t-Bu)), sodium methoxide ($NaOCH_3$), sodium hydride (NaH), trimethylamine, trimethylamine, N,N-dimethylethanolamine, N,N-dimethylcyclohexylamine and higher N,N-dimethylalkylamines, N,N-dimethylaniline, N,N-dimethylbenzylamine, N,N,N'N'-tetramethylethylenediamine, N,N,N',N'',N'''-pentamethyldiethylenetriamine, imidazole, N-methylimidazole, 2-methylimidazole, 2,2-dimethylimidazole, 4-methylimidazole, 2,4,5-trimethylimidazole and 2-ethyl-4-methylimidazole. In a preferred embodiment, the base is selected from the group consisting of lithium hydroxide, sodium hydroxide and potassium hydroxide.

In various embodiments, reacting the diepoxide with the modified sugar moiety occurs in a solvent mixture comprising methanol and water.

In various embodiments, mixing the poly(ethylene imine) and the at least one monomer is controlled by changing the feed ratio of the poly(ethylene imine) and the at least one monomer. In various embodiments, the feed ratio is about 10 to about 240, about 10 to about 97, preferably about 20 to about 70, and more preferably about 22, about 41, about 53 or about 65. Advantageously, no or minimal precipitation is formed when the feed ratio is about 10 to about 97. This may be due to the monomers of the polymer of the present invention. In particular, this may be because of the absence of protecting groups on at least one of the hydroxyl groups of the modified sugar moiety.

In contrast, prior art polymers may lead to significant amounts of precipitation when deprotection of the hydroxyl groups of the modified sugar moiety is carried out. Specifically, when galactose-functionalized PEI polymers were synthesized by grafting various cyclic carbonate monomers with pendent acetal protecting galactose groups (MTC-ipGal) to PEI via nucleophilic addition, a lot of precipitation was observed in the acidic hydrolysis step when the feed ratio of MTC-ipGal to PEI was beyond 25. Furthermore, the amount of precipitate increased with increasing the feed ratio. This may be due to the incomplete deprotection of the hydroxyl groups of modified galactose during deprotection via acidic hydrolysis. Besides MTC-ipGal, when epoxy-ipGal was grafted to PEI via nucleophilic addition, the protecting groups such as acetal, could not be fully removed at the high molar ratio of MTC-ipGal to PEI after deprotection via acidic hydrolysis.

In another aspect of the invention, there is provided a complex comprising a biologically active material and a polymer as described above. Advantageously, the complex does not exhibit reduced transfection efficiency with increasing N/P ratio, does not exhibit significantly lowered transfection efficiency than unmodified PEI and the size of the complex is desirable for in vivo applications. In various embodiments, the size of the complex is in the range of about 20 nm to about 200 nm.

In contrast, prior art complexes demonstrated reduced transfection efficiency with increasing N/P ratio within the range of N/P ratio of 2 to 10 and the transfection efficiency was lower than that of pristine PEI from N/P ratio of 6 onwards in HepG2 cells.

In various embodiments the biologically active material is a nucleic acid, preferably a gene. The gene may be selected from the group consisting of siRNA, mRNA and plasmid DNA. Advantageously, the polymer can be more efficient at delivering a gene compared to prior art polymers comprising PEI. More advantageously, the complex may be less cytotoxic at high N/P ratios compared to prior art polymers comprising PEI.

In another aspect of the invention, there is provided a method of treating a cell comprising contacting a cell with the complex as described above.

In various embodiments the method is in vitro or in vivo.

In various embodiments the cell is a hepatic cell.

In another aspect of the invention, there is provided a complex as described above for use in a treatment, preferably the use is in the treatment of cancer or other diseases caused by a genetic disorder.

In various embodiments the complex is used in the treatment for liver cancer.

In another aspect of the invention, there is provided use of the complex as described above in the manufacture of a medicament for the treatment of cancer, wherein the cancer is liver cancer.

Examples

Non-limiting examples of the present disclosure will be further described, which should not be construed as in any way limiting the scope of the disclosure.

Chemicals

All chemicals were bought from Sigma-Aldrich and used as received unless especially mentioned. Branched PEI (Mn 10,000, Mw 25,000) was freeze-dried under high vacuum overnight prior to use. 1,7-Octadiene diepoxide was purchased from Tokyo Chemical Industry Co. Ltd.

Characterization by $^1H$ NMR Spectroscopy

The $^1H$ NMR measurements were performed using a Bruker Advance 400 MHz NMR spectrometer with an acquisition time of 3.2 s, a pulse repetition time of 2.0 s, a 30° pulse width, 5208-Hz spectral width, and 32 K data points. Chemical shifts were referred to the solvent peaks (δ=7.26 ppm for $CDCl_3$, 2.50 ppm for DMSO-$d^6$ and 4.70 ppm for $D_2O$).

Cell Culture

Hep3B cells were cultured in Dulbecco's Modified Eagle Medium (DMEM, Invitrogen, Singapore). All media were supplemented with 10% (v/v) fetal bovine serum (FBS, Invitrogen, Singapore), streptomycin at 100 µg/mL, penicillin at 100 U/mL, and L-glutamine at 2 mM (Sigma-Aldrich, Singapore). Cells were cultured at 37° C., under an atmosphere of 5% $CO_2$ and 95% humidified air. All cell lines were split using Trypsin/EDTA medium when reached 90% confluence.

Example 1: Monomer Synthesis

Figure 1:
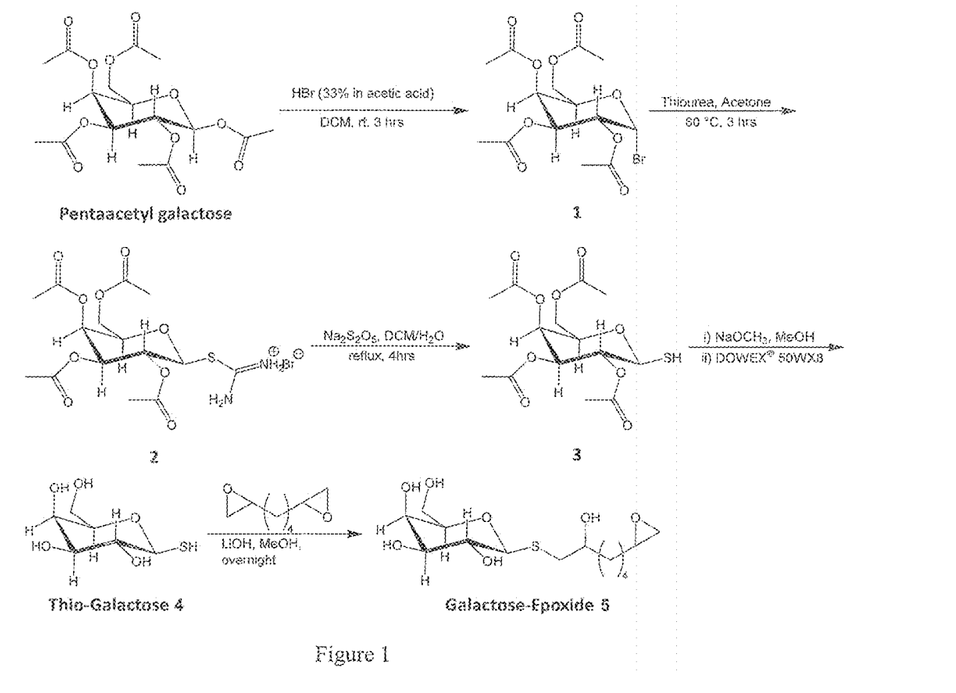
FIG. 1 illustrates the synthesis of a monomer, Galactose-Epoxide, in accordance with an embodiment of the present invention.

The synthetic procedure for preparation of a monomer is given using galactose-epoxide as a typical example and is illustrated in FIG. 1.

Synthesis of 2,3,4,6-Tetra-O-acetyl-α-D-galactopyranosyl bromide (1)

1,2,3,4,6-Pentaacetyl galactose (20.0 g, 51.2 mmol) was dissolved in dichloromethane (DCM) (120 mL), and hydrogen bromide (33% in acetic acid, 150 mL) was then added to this solution. The reaction mixture was stirred under $N_2$ atmosphere (i.e. inert conditions) at room temperature for 3 hours. After 3 hours, the reaction mixture was partitioned between DCM (100 mL) and water (100 mL) and the aqueous phase was re-extracted with DCM (3×50 mL). The combined organic DCM phases were washed with sodium hydrogen carbonate until pH 8 was obtained, stirred for several hours until no bubbles were produced, and the phases were separated. The organic layer was washed with brine (3×100 mL), dried over magnesium sulphate ($MgSO_4$), filtered and concentrated in vacuo to afford 2,3,4,6-tetra-O-acetyl-α-D-galactopyranosyl bromide 1 (18.9 g, 90%) as a yellow oil.

Synthesis of 2,3,4,6-Tetra-O-acetyl-β-D-galactopyranosyl-1-isothiouronium bromide (2)

2,3,4,6-Tetra-O-acetyl-α-D-galactopyranosyl bromide 1 (18.9 g, 46 mmol) and thiourea (5.3 g, 68.9 mmol) were dissolved in acetone (50 mL) and heated at 60° C. under $N_2$ atmosphere for 3 hours. After 3 hours, the reaction mixture was concentrated in vacuo. Crystallization from acetone/hexane afforded 2,3,4,6-tetra-O-acetyl-f-D-galactopyranosyl-1-isothiouronium bromide 2 (13.52 g, 61%) as a white solid.

Synthesis of 2,3,4,6-Tetra-O-acetyl-1-thio-β-D-galactopyranose (3)

2,3,4,6-tetra-O-acetyl-β-D-galactopyranosyl-1-isothiouronium bromide 2 (13.52 g, 27.8 mmol) and sodium metabisulfite (7.5 g, 39.1 mmol) were added to a mixture of DCM (60 mL) and water (60 mL) under stirring. The mixture was heated to reflux under $N_2$ atmosphere for 4 hours. After 4 hours, the reaction mixture was cooled to room temperature, and the phases were separated. The aqueous layer was re-extracted with DCM (3×100 mL). The combined organic layers were washed with water (2×50 mL), brine (2×50 mL), dried over $MgSO_4$, filtered and concentrated in vacuo to afford 2,3,4,6-tetra-O-acetyl-1-thio-β-D-galactopyranose 3 (9.92 g, 90%) as a pale yellow oil.

Synthesis of 1-Thio-β-D-galactose (Thio-Galactose) (4)

2,3,4,6-tetra-O-acetyl-1-thio-β-D-galactopyranose 3 (1.5 g, 4.05 mmol) was dissolved in dry methanol (10 mL), and sodium methoxide solution (25 wt. % in methanol, 1.75 mL) was added to the solution. The reaction mixture was stirred at room temperature for 10 min before the mixture of methanol (10 mL) and de-ionized (DI) water (10 mL) was added. The reaction mixture was then acidified with DOWEX® 50WX8-200 (about 3.5 g) to adjust its pH value to 5-6, filtered and concentrated in vacuo, and freeze-dried to afford 1-thio-β-D-galactose (Thio-Galactose) 4 (0.8 g, ~100%) as a white sticky solid.

Synthesis of Galactose-Epoxide (5)

Thio-Galactose 4 (1.92 g, 9.8 mmol) was dissolved in a mixture of DI water (4 mL) and methanol (8 mL), to which 1,7-octadiene diepoxide (7.29 mL, 49 mmol) and lithium hydroxide (LiOH) (117.6 mg, 4.9 mmol) were added. More DI water and methanol were added to the mixture to achieve a homogeneous solution. The solution was stirred overnight and then precipitated in a mixture of tetrahydrofuran (THF) and diethyl ether ($Et_2O$) (THF: $Et_2O$=2:1 by volume), centrifuged, washed with a mixture of THF and $Et_2O$ (THF: $Et_2O$=2:1 by volume), and dried in vacuo to afford galactose-epoxide 5 (2.55 g, 75%) as a white sticky solid.

Example 2: Polymer Synthesis

Figure 2:
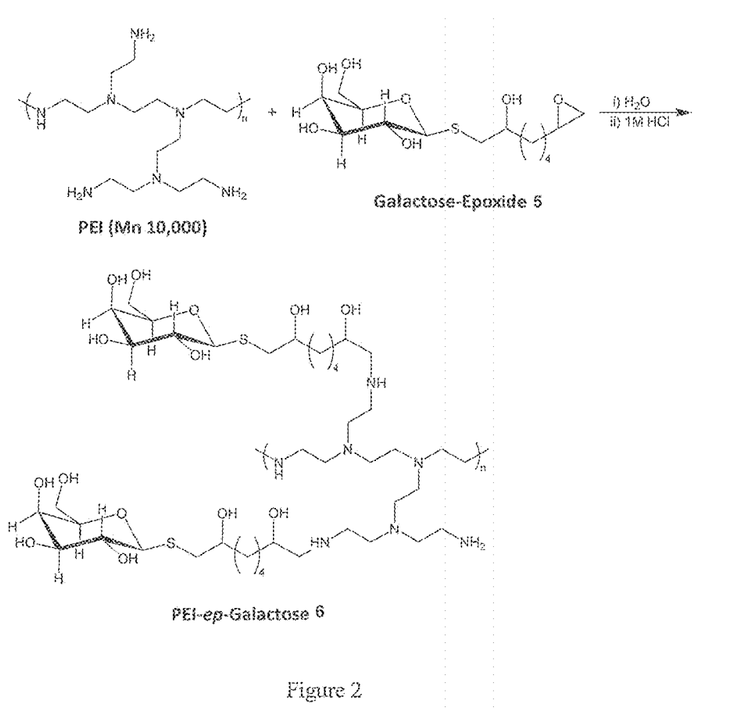
FIG. 2 illustrates the synthesis of a polymer, PEI-Galactose, in accordance with an embodiment of the present invention.

The synthetic procedure for preparation of a polymer is given using PEI-Galactose as a typical example and is illustrated in FIG. 2.

Synthesis of PEI-Galactose (6)

Galactose-epoxide 5 (0.32 g, 0.95 mmol) and PEI (78.9 mg, 7.89×10$^{-3}$ mmol) were dissolved in 4 mL of DI water, and the solution was heated at 70° C. and stirred overnight. The solution was then cooled down to room temperature and acidified with 1 M HCl solution (8 mL). The product was then purified by ultra-centrifugation (molecular weight cutoff: 2 kDa), washed with DI water three times and freeze-dried to afford PEI-Galactose 6 (0.2 g, 79%) as a white solid.

As shown in Examples 1 and 2 above, a series of PEI-galactose was synthesized, wherein a number of galactose groups without protecting groups could be directly grafted to PEI using a diepoxide linker.

To install the epoxide linkage and as illustrated in FIG. 1, Thio-Galactose 4 was firstly synthesized via a four-step reaction. Galactose-Epoxide 5 was subsequently achieved by conjugating a 1,7-octadiene diepoxide to Thio-Galactose 4 via ring-opening nucleophilic addition in the presence of LiOH as a catalyst. To ensure only one epoxy group of diepoxide was involved in the conjugation reaction and the other one was left for the further PEI conjugation, a large excess of 1,7-octadiene diepoxide (5 times relative to Thio-Galactose) was used, and the unreacted diepoxide was removed by precipitation in a mixture of tetrahydrofuran (THF) and diethyl ether ($Et_2O$) (THF: $Et_2O$=2:1 by volume).

Finally, Galactose-Epoxide 5 was directly grafted to PEI to afford PEI-Galactose 6 without any catalyst (FIG. 2). The various substitution of galactose was obtained by changing the feed ratio of Galactose-Epoxide 5 to PEI and reaction temperature, and unreacted Galactose-Epoxide 5 in the reaction was removed by ultrafiltration in a Vivaspin 20 concentrator (MWCO=2 kDa, Sartorius AG, Goettingen, Germany). Quantitative comparisons between the integral intensities of butamethylene peaks of the diepoxide and those of the hydrogen peaks attributed to PEI, galactose and the rest methylene and methine groups of the diepoxide gave the compositions of the polymers (FIG. 2). The $^1$H NMR analysis showed that the content of galactose in the polymers was proportional to that in the feed when the molar ratio was low i.e when the feed ratio of Galactose-Epoxide to PEI is less than or equal to 10, or less than or equal to 9, or less than or equal to 8, or less than or equal to 7, or less than or equal to 6, or less than or equal to 5. However, this relationship was not present when the molar ratio was high i.e when the feed ratio of Galactose-Epoxide to PEI is greater than 10.

Example 3: Preparation, Particle Size and Zeta Potential Analyses of Polymer/Nucleic Acid Complexes PEI-Galactose 6 was first dissolved in DNase/RNase-free water (Fermentas, Singapore) to form a polymer solution. To form the complexes, an equal volume of DNA solution was dripped into the polymer solution to achieve the intended NIP ratios (molar ratio of nitrogen content in the polymer to the phosphorus content of the nucleic acids) under gentle vortexing for about 5 s. The mixture was equilibrated at room temperature for 30 min to allow complete electrostatic interaction between the polymer and the nucleic acids, before being used for subsequent studies. The particle sizes and zeta potentials of the post-equilibrated polymer/DNA complexes were measured by dynamic light scattering using the Zetasizer (Malvern Instrument Ltd., Worcestershire, UK). Immediately prior to the measurement, the polymer/DNA complexes in nuclease free water was diluted 10× in PBS to mimic the dilution in the physiological environment after intravenous (iv) administration. Particle size and zeta potential measurements were repeated for 3 runs per sample and reported as the mean±standard deviation of 3 readings.

Figure 3:
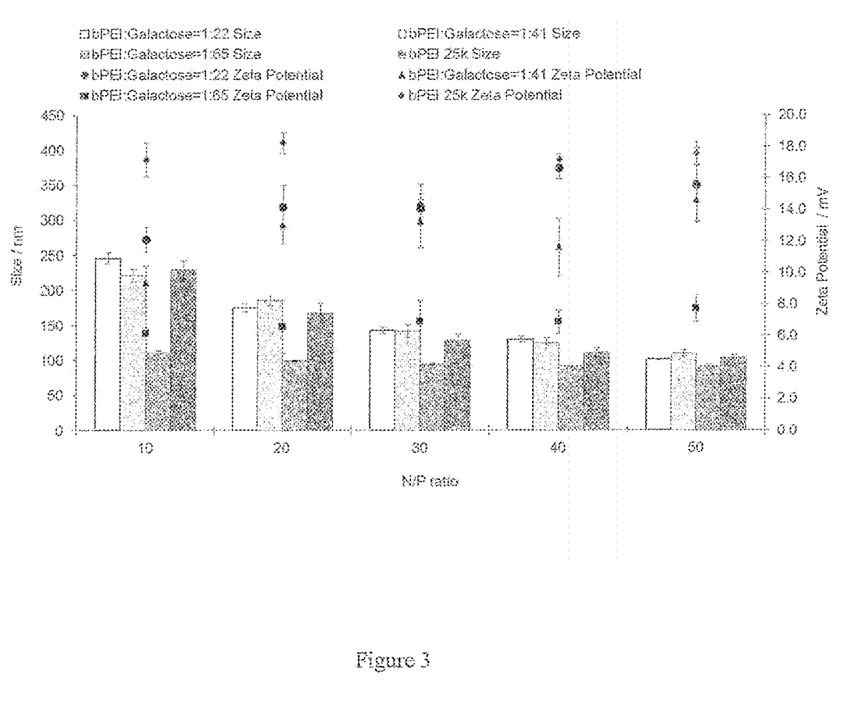
FIG. 3 illustrates the particle size and zeta potential of polymer/DNA complexes at various N/P ratios.

Small size of nanoparticles within the nano-size range is desirable in drug and gene delivery, as small nanoparticles can take advantage of the presence of 100-200 nm fenestrations along the sinusoidal endothelial wall which permit the extravasation of nanoparticles less than 200 nm into the liver. Moreover, in the case of carcinoma, passive accumulation of the nanoparticles less than 400-600 nm can occur in the tumor via the enhanced permeation and retention (EPR) effect. Also, particle size is an important parameter for dictating cellular uptake by non-specific endocytosis. Nanoparticle sizes under 200 nm were obtained, which is considered desirable. As can be seen from FIG. 3, the size of the DNA complexes generally decreased with increasing N/P ratio, indicating that stronger electrostatic interaction between the cationic polymer and anionic DNA enabled the formation of more compact complexes. This effect was more prominent in bPEI:Galactose=1:22/DNA, bPEI:Galactose=1:41/DNA and bPEI/DNA complexes, whose sizes were over 246, 221 and 229 nm when the N/P ratio was 10, but plunged to a particle size of 101, 110 and 103 nm respectively when the N/P ratio was 50. Size of bPEI:Galactose=1:65 decreased from 110 nm when the N/P ratio was 10 to 91 nm when the N/P ratio was 50, thereby achieving a particle size within the desired nano-size range. The size distribution of the polymer/DNA complexes was found to be narrow with polydispersity of 0.04-0.16.

The net positive charge of DNA complexes also has a crucial function of interacting with the negatively charged phospholipid surface of the cell membrane, therefore affecting cellular uptake as well as gene transfection efficiency. From FIG. 3, bPEI/DNA demonstrated the highest surface charge of 17-18 mV, while galactose functionalized bPEI showed lower cationic charge density at N/P 10-50, with lower zeta potential, corresponding to higher galactose conjugation ratio (Zeta potential: ~12-17 mV for bPEI:Galactose=1:22/DNA, ~9-15 mV for bPEI:Galactose=1:41/DNA, ~6-8 mV for bPEI:Galactose=1:65/DNA). Because positively charged particles are prone to plasma protein and erythrocyte adhesion, which might cause alternative complement pathway activation, limiting in vivo applications, slightly lower zeta potentials demonstrated by these modified bPEI/DNA complexes at N/P 10-50 were expected to exert less cytotoxicity as compared to the unmodified PEI.

Example 4: Cytotoxicity Assay

The cytotoxicity of the polymer/DNA complexes was studied in Hep3B cell line using the standard MTT assay. Briefly, Hep3B cells were seeded onto 96-well plates at densities of 10000 cells per well and allowed to grow to 70% confluency before treatment. Polymer/DNA complexes at various N/P ratios were prepared in water as described earlier. The cells in each well were then incubated with sample-containing growth media comprising of 10 μL of polymer/DNA complexes and 100 μL of fresh media for 4 h at 37° C. Following incubation, the wells were replaced with fresh growth media and incubated further for 68 h. Subsequently, 100 μL of growth media and 20 μL of MTT solution (5 mg/ml in PBS) were then added to each well and the cells were incubated for 4 h at 37° C. according to the manufacturer's directions. Resultant formazan crystals formed in each well were solubilized using 150 μL of DMSO upon removal of growth media. A 100 μL aliquot from each well was then transferred to a new 96-well plate for determination of absorbance using a microplate spectrophotometer at wavelengths of 550 nm and 690 nm. Relative cell viability was expressed as $[(A550-A690)_{sample}/(A550-A690)_{control}]\times 100\%$. Data are expressed as mean±standard deviations from two independent experiments performed in eight replicates per N/P ratio.

Figure 4:
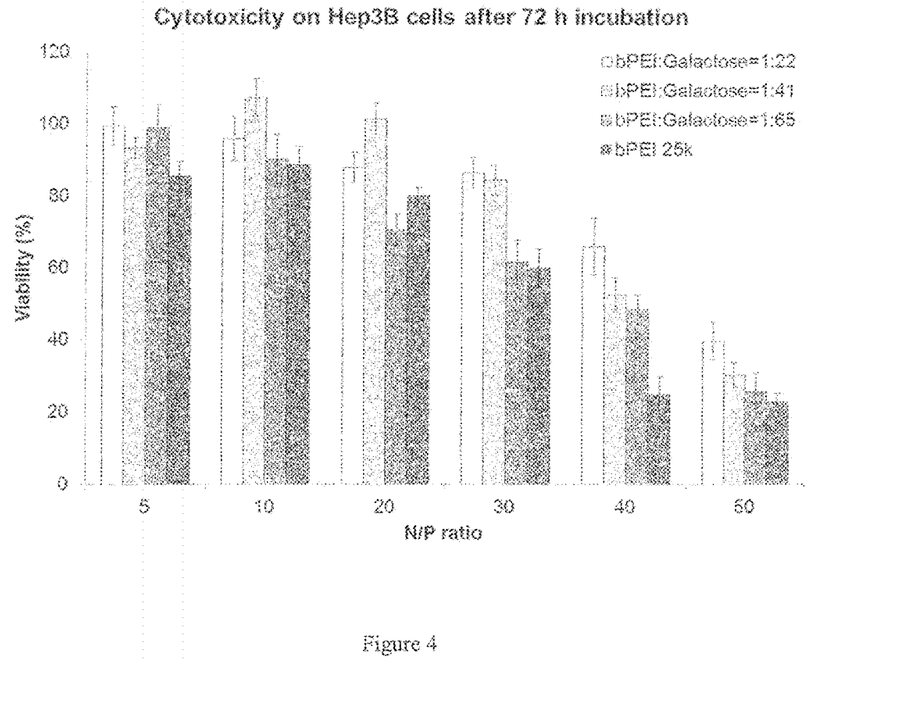
FIG. 4 illustrates the viability of Hep3B cells after incubation with polymer/DNA complexes at various N/P ratios for 72 h in comparison to unmodified bPEI/DNA complexes. Results represent mean±standard deviation of at least 8 replicates.

The cytotoxicity of unmodified bPEI was likely due to polymer aggregation on cell surfaces, impairing important membrane functions, as PEI has been reported to induce holes formation or expand the size of pre-existing holes on the cellular membrane. The strong positive charge of PEI has been considered to be the main culprit of its high cytotoxicity. In order to evaluate the cytotoxicity of the polymer/DNA complexes, MTT assay was performed on Hep3B cells. The luciferase plasmid was used for complex formation. As can be seen from FIG. 4, the viability of Hep3B cells treated with unmodified PEI/DNA complexes drastically plunged with increasing PEI concentration (or N/P ratio), yielding cell viability of less than 25% at N/P 40 and above. However, all the modified PEI/DNA complexes were less cytotoxic than unmodified bPEI/DNA complexes at N/P 40. At N/P 40, the viability of the cells treated with bPEI:Galactose=1:22/DNA, bPEI:Galactose=1:41/DNA and bPEI:Galactose=1:65/DNA complexes was 66%, 52% and 48% respectively. Moreover, bPEI:Galactose=1:22/DNA and bPEI:Galactose=1:41/DNA were significantly less toxic than unmodified bPEI/DNA complexes at N/P 20-50.

Example 5: In Vitro Gene Expression

The in vitro gene transfection efficiency of the polymer/DNA complexes was investigated using Hep3B. Cells were seeded onto 24-well plates at a density of $1\times10^5$ cells per 500 µl per well for luciferase gene delivery. After 24 h, the plating media were replaced with fresh growth media, followed by the drop-wise addition of 50 µL of the complex solution (containing 2.5 µg luciferase plasmid DNA) at various N/P ratios. Following 4 h of incubation, free complexes were removed by replacing the medium in each well. After a further 68 h of incubation, the cell culture medium in each well was removed and the cells were rinsed once with 0.5 mL of phosphate-buffered saline (PBS, pH 7.4). For luciferase expression assay, 0.2 mL of reporter lysis buffer (1x) was added to each well. The cell lysate collected after two cycles of freezing (−80° C., 30 min) and thawing (room temperature, 30 min) was cleared by centrifugation at 14000 rpm for 5 min. After that, 20 µL of supernatant was mixed with 100 µL of luciferase substrate for the determination of relative light units (RLU) using a luminometer (Lumat LB9507, Berthold, Germany). The RLU readings were normalized against the protein concentration of the supernatant determined using the BCA protein assay to give the overall luciferase expression efficiency. In all in vitro gene expression experiments, naked DNA was used as a negative control. Data were expressed as mean±standard deviations of triplicates.

Figure 5:
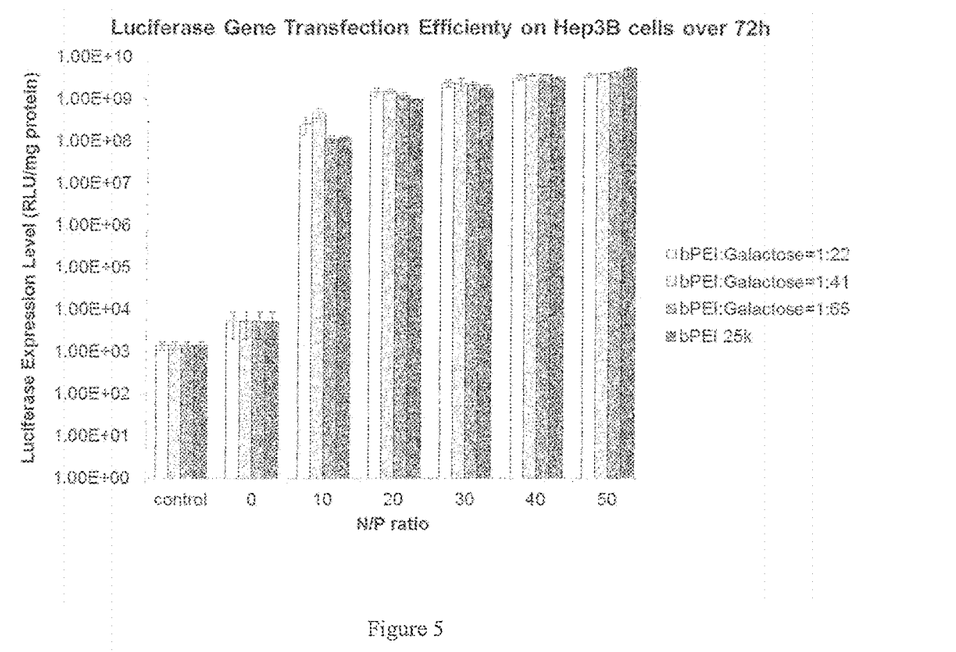
FIG. 5 illustrates the in vitro luciferase expression levels in Hep3B cells, mediated by polymers at various N/P ratios indicated. Results represent mean±standard deviation of triplicates.

Luciferase gene expression assay detects the mean protein expression level in the transfected cells and therefore is an important parameter for evaluation of the gene transfection efficiency of the polymers. As shown in FIG. 5, at cell viability of 80% or higher, the highest gene transfection efficiency induced by unmodified bPEI/DNA complexes was achieved at N/P 20, which is significantly lower than that obtained by bPEI:Galactose=1:22/DNA and bPEI:Galactose=1:41/DNA complexes at N/P 30. The superior performance of galactose functionalized polymers was due to the fact that there are abundant asialoglycoprotein receptors (ASGP-Rs) on the cell surface of Hep3B (human liver cancer cell line), which bind galactose preferably and favour the uptake of the nanoparticles by receptor mediated endocytosis.

To confirm that the enhanced luciferase gene expression induced by the galactose-modified bPEI/DNA complexes was indeed mediated through the ASGP-R, Hep3B cells were pre-treated with pure galactose (2 mg/mL) for 1 h before gene transfection. It is evident from FIG. 4 that pre-treatment of Hep3B with galactose for 1 h resulted in a significant decrease in the luciferase gene expression mediated by bPEI:Galactose=1:22/DNA and bPEI:Galactose=1:41/DNA complexes for all the N/P ratios tested. Reduction of gene expression for bPEI:Galactose=1:65/DNA was not significant especially at N/P ratios of 30 or below, where the DNA complexes have negligible cytotoxicity. This might be because the amount of galactose used for the competition assay was not enough to compete with bPEI:Galactose=1:65/DNA complexes with a higher number of galactose groups. Gene expression induced by the unmodified bPEI/DNA complexes, on the other hand, was not significantly affected by incubation with galactose. Therefore, these results strongly suggest that the higher luciferase gene expression induced by the bPEI:Galactose/DNA complexes could be attributed to the recognition and binding of the galactose residues on the exterior of the complexes by the ASGP-Rs on the surface of the Hep3B cells, leading to enhanced cellular uptake possibly through the receptor-mediated endocytotic pathway.

Example 6: Galactose Competition Assay

Hep3B cells were seeded onto 24-well plates at a density of $1\times10^5$ cells per well. After 24 h, the cells were pre-incubated with 2 mg/ml of Galactose (Sigma Aldrich, Singapore) in 500 µL of fresh media per well for 1 h before 50 µL of galactose-functionalized bPEI/DNA complexes were added and allowed to transfect for 4 h. After the 4 h incubation, the transfection medium was replaced with fresh media and the luciferase expression levels were analysed as described above after a further incubation of 68 h.

It will be apparent that various other modifications and adaptations of the invention will be apparent to the person skilled in the art after reading the foregoing disclosure without departing from the spirit and scope of the invention. It is intended that all such modifications and adaptations come within the scope of the appended claims. Further, it is to be appreciated that features from various embodiment(s), may be combined to form one or more additional embodiments.

The invention claimed is:

1. A polymer comprising a poly(ethylene imine) and at least one monomer, each monomer of the at least one monomer comprising:
   (a) a modified sugar moiety comprising a sugar moiety wherein at least one hydroxyl group of the sugar moiety is substituted with a sulphur atom or a nitrogen atom to form the modified sugar moiety; and
   (b) a chemical moiety comprising a terminal epoxide linking the poly(ethylene imine) to the at least one monomer; and
   wherein the sulphur atom or nitrogen atom links the modified sugar moiety to the chemical moiety.

2. The polymer of claim 1, wherein the polymer is water-soluble.

3. The polymer of claim 1, wherein the chemical moiety is derived from a diepoxide selected from the group consisting of cyclooctene diepoxide, divinylbenzene diepoxide, 1,7-octadiene diepoxide, 1,3-butadiene diepoxide, 1,4-pentadiene diepoxide, 1,5-hexadiene diepoxide, 1,6-heptadiene diepoxide and the diepoxide of 4-cyclohexenecarboxylate 4-cyclohexenylmethyl ester.

4. The polymer of claim 1, wherein the modified sugar moiety is one or more selected from the group consisting of modified mannose, modified galactose, and modified glucose.

5. A method of synthesizing a polymer, the method comprising mixing a poly(ethylene imine) and at least one monomer, each monomer of the at least one monomer comprising a modified sugar moiety comprising a sugar moiety wherein at least one hydroxyl group of the sugar moiety is substituted with a sulphur atom or a nitrogen atom to form the modified sugar moiety and a chemical moiety comprising a terminal epoxide linking the poly(ethylene imine) to the monomer; and wherein the sulphur atom or the nitrogen atom links the modified sugar moiety to the chemical moiety.

6. The method of claim 5, wherein the modified sugar moiety comprises at least one hydroxyl group, and wherein at least one of the hydroxyl groups is a free hydroxyl group.

7. The method of claim 5, wherein the method does not require deprotection.

8. The method of claim 5, wherein a catalyst is not used.

9. The method of claim 5, further comprising acidification.

10. The method of claim 5, wherein the at least one monomer is synthesized by reacting a diepoxide with the modified sugar moiety.

11. The method of claim 10, wherein a base is used as a catalyst and wherein the base is selected from the group consisting of lithium hydroxide, sodium hydroxide and potassium hydroxide.

12. The method of claim 10, wherein reacting the diepoxide with the modified sugar moiety occurs in a solvent mixture comprising methanol and water.

13. The method of claim 10, wherein the diepoxide is selected from the group consisting of cyclooctene diepoxide, divinylbenzene diepoxide, 1,7-octadiene diepoxide, 1,4-pentadiene diepoxide, 1,3-butadiene diepoxide, 1,5-hexadiene diepoxide, 1,6-heptadiene diepoxide and the diepoxide of 4-cyclohexenecarboxylate 4-cyclohexenylmethyl ester.

14. The method of claim 5, wherein mixing the poly(ethylene imine) and the at least one monomer is controlled by changing the molar feed ratio of the poly(ethylene imine) and the at least one monomer.

15. The method of claim 14, wherein the molar feed ratio is about 10 to about 97.

16. The polymer of claim 1, wherein the modified sugar moiety comprises
(a) at least one hydroxyl group, and wherein at least one of the hydroxyl groups is a free hydroxyl group; or
(b) at least one hydroxyl group, and wherein all of the hydroxyl groups are free.

17. The polymer of claim 1, wherein the poly(ethylene imine) is
(a) a branched poly(ethylene imine); or
(b) linked to about 10 to about 97 monomers.

18. The method of claim 5, wherein the mixing of the poly(ethylene imine) and the at least one monomer:
(a) occurs in an aqueous solvent;
(b) occurs at about 70° C.; or
(c) does not require an inert atmosphere.

19. The polymer of claim 1, formed in a complex with a biologically active material, wherein the biologically active material is a nucleic acid.

20. A method of treating a cell comprising contacting the cell with the complex of claim 19, wherein the method is in vitro or in vivo.

* * * * *